United States Patent [19]
Camplin et al.

[11] Patent Number: 5,763,786
[45] Date of Patent: Jun. 9, 1998

[54] AUTOMATED MILL ROLL INSPECTION SYSTEM

[75] Inventors: Kenneth R. Camplin, Forest; Dennis D. Lang, Lynchburg; Darrel P. Kohlhorst, Goode; Daniel P. Geier, Forest; Sean M. Fitzpatrick, Good; Bradley E. Cox; Richard C. Brewer, both of Lynchburg; Thomas A. Artman, Moneta; Daniel T. MacLauchlin, Lynchburg, all of Va.

[73] Assignee: The Babcock & Wilcox Company, New Orleans, La.

[21] Appl. No.: 715,673

[22] Filed: Sep. 18, 1996

[51] Int. Cl.[6] .......................... G01N 29/10; G01N 29/24
[52] U.S. Cl. .................. 73/643; 73/622; 364/507; 364/552
[58] Field of Search ................. 73/602, 620, 622, 73/627, 643; 364/507, 552, 551.01; 324/227, 238

[56] References Cited

U.S. PATENT DOCUMENTS

| | | | |
|---|---|---|---|
| 4,058,002 | 11/1977 | Moran | 73/620 |
| 4,296,486 | 10/1981 | Vasile | 73/643 |
| 4,372,163 | 2/1983 | Tittman et al. | 73/602 |
| 4,423,636 | 1/1984 | Plante | 73/622 |
| 4,495,587 | 1/1985 | Plante et al. | 73/602 |
| 4,765,750 | 8/1988 | Wadley | 374/137 |
| 5,085,082 | 2/1992 | Cantor et al. | 73/622 |
| 5,433,133 | 7/1995 | Andoh et al. | 73/622 |
| 5,439,157 | 8/1995 | Geier et al. | 228/9 |
| 5,469,743 | 11/1995 | Zorn | 73/627 |
| 5,474,225 | 12/1995 | Geier et al. | 228/102 |
| 5,537,876 | 7/1996 | Davidson et al. | 73/624 |

OTHER PUBLICATIONS

Disclosure of Physical Machine and Product Information at AISE Convention, Pittsburgh, PA. Sep. 25, 1995.

*Primary Examiner*—Hezron E. Williams
*Assistant Examiner*—Rose M. Miller
*Attorney, Agent, or Firm*—Daniel S. Kalka; Robert J. Edwards

[57] ABSTRACT

An EMAT inspection system is utilized on a mill roll to identify surface and sub-surface defects such as firecracks in steel mill rolls with the results being displayed on a remote screen of a display and control system which also records the inspection results and controls the EMAT system.

8 Claims, 3 Drawing Sheets

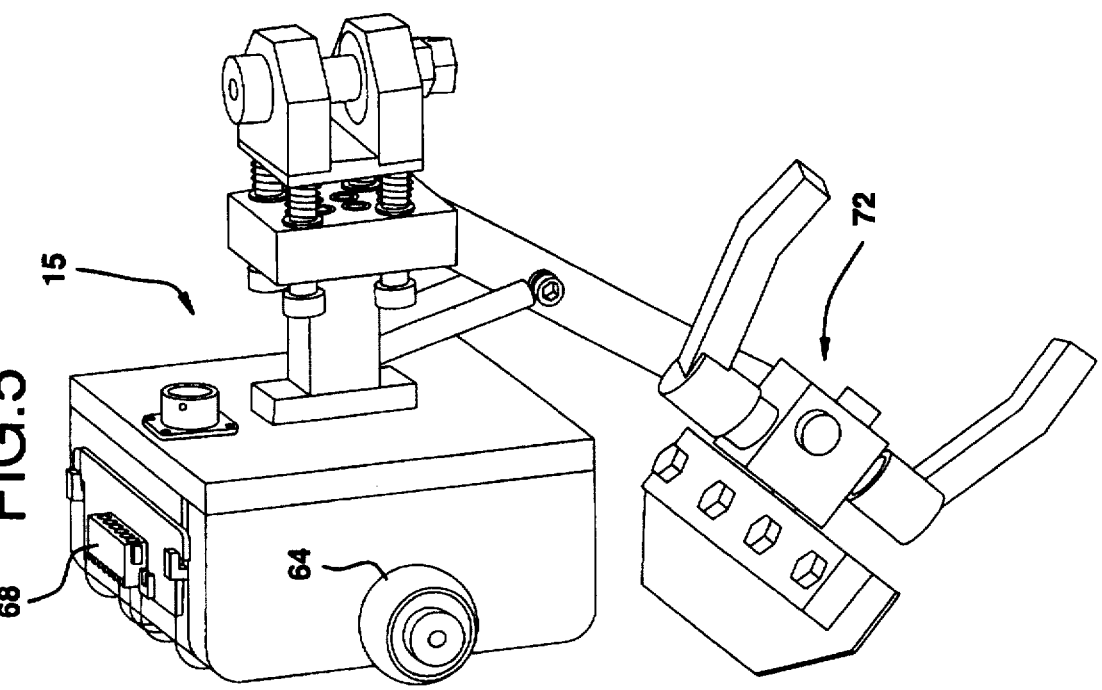
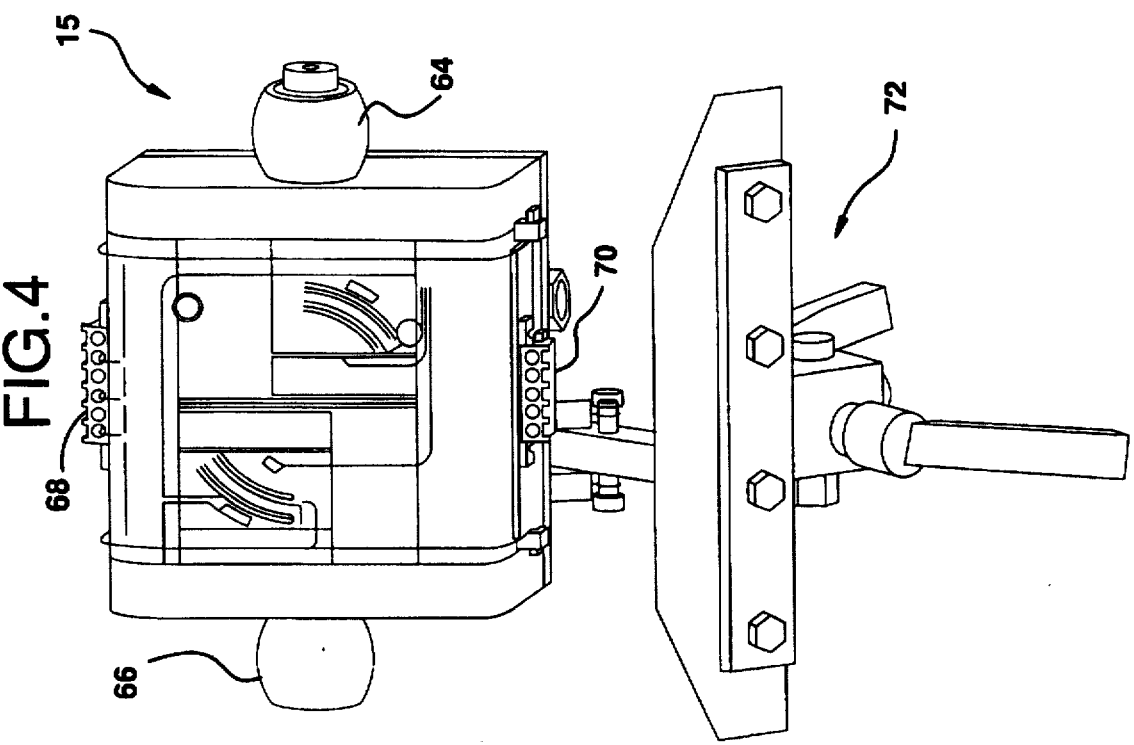

1
AUTOMATED MILL ROLL INSPECTION SYSTEM

BACKGROUND OF THE INVENTION

1. Field of the Invention

The present invention relates in general to an automated system for non-destructive inspection of metal through the use of EMAT (electromagnetic acoustic transducer) technology and more specifically to the use of such systems to detect surface and sub-surface cracks in mill rolls of forged or cast metal.

2. Description of the Related Art

A variety of industries use sheet metal which is produced typically at a factory from slabs processed by a rolling mill. Slabs are heated and rolled by the mill into a long flat sheet which is then wound into a coil at the end of the mill. Thereafter, the coil is removed from the mill and shipped to other sections of the factory where further treatment processes are performed. To make these other processes have fewer interruptions, the coil is unrolled and joined at one of its ends to the end of another coil by an electric resistance weld which generally is in the form of a butt weld. Any number of coils may be welded together in such fashion, depending on the desired length of process run.

In order to identify and remedy weld defects before they can cause breaks and consequential production problems, non-destructive testing of the welds is performed shortly after they have been made using an EMAT system disclosed in U.S. Pat. No. 5,439,157 which is arranged to transmit and receive SH shear waves. The SH shear waves are launched by a transmitter meander coil, and the waves travel through the sheet metal to the weld where they are reflected back through the sheet metal and are received by a separate receiver meander coil EMAT located near the transmitter. During this non-destructive test, the reflected wave produces an electrical signal in the receiver coil, which is monitored while both the transmitter coil and the receiver coil are scanned close to the surface of the sheet metal, parallel to the weld line, and over the full width of the sheet metal. During the scanning, the amplitude of the signal produced in the receiver coil is measured and used to indicate the quality of the weld.

However, there is still a need for a method and apparatus which reliably detects surface and near surface defects which can occur in a mill roll during its forming a slab into a coil of sheet metal, or during its cold reduction of the sheet metal thickness. Preferably such a system would be a fully automated mill roll inspection system and permit a fast roll inspection cycle time.

SUMMARY OF THE INVENTION

The present invention is directed to solving the problems associated with prior art mill roll inspection systems as well as others by providing a new and improved system for non-destructive inspection of surface and sub-surface firecracks and spalling in a mill roll through the use of ultrasonic surface waves. The present invention has among its principal novel features the ability to automatically position a sensor apparatus containing EMAT (electromagnetic acoustic transducer) transmitter and receiver coils along the surface of a mill roll to thus scan the entire roll surface, receive, record, monitor and analyze the electrical signal produced in the receiver coil by the transmitted surface wave to indicate the presence of a defect such as a crack in the roll surface, near surface, or sub-surface, and communicate electronically with the mill roll apparatus to rotate and translate the roll for complete roll inspection.

The present invention replaces the need for conventional eddy current and ultrasonic inspection systems by combining the ability to detect both surface breaking and subsurface flaws into one inspection operation. The advantages include significantly improved performance, reliability and efficiency of the mill roll process and elimination of the need for an inspection operator.

The present invention, also referred to as Temate® 5500, offers two modes to be used by the inspection apparatus to accomplish the detection of the above described surface and sub-surface defects such as firecracks or spalling of the mill roll. The "fine" mode offers high crack detection capabilities in the top 0.020" depth of the mill roll surface. The "deep" mode offers crack detection up to 0.250" into the mill roll material.

This deep mode offers a unique capability to do a quick check of the roll to determine if grinding alone will pass the roll if surface defects are present. If the "deep" inspection mode detects a crack and provides an approximate depth or minimum clean-up depth, the roll can be knowingly deferred to lathe operations since grinding would be too time consuming to cure the defect. If no crack is detected in the "deep" mode, then the normal grinding finishing operations can be performed followed by the "fine" scan to verify that the resulting roll surface is free of any defects.

The present invention automatically controls the operation of the sensor apparatus and coordinates the mentioned surface and sub-surface inspections. The present EMAT inspection system is situated above the mill roll as the roll is fixtured in a grinding or turning machine, and uses a computer control unit which is instrumental in providing automated control of the entire apparatus. The computer control unit has an electrical interface with the controller of the mill roll grinder, as well as, with the plant host computer, and has a data acquisition device. The interface to the controller of the mill roll apparatus is used to coordinate the sequence by which the inspection process is actuated. At the conclusion of each test, signals are received by the computer control unit from the mill roll sensor apparatus. These signals are used to coordinate the described non-destructive test processes.

It is also an object of the present invention to eliminate the need under the prior art to rely on manual and subjective review of non-destructive test results recorded on a strip chart recorder. To achieve this object, a data acquisition unit is included in the present invention. The data acquisition unit acquires, displays, stores and analyzes real-time machine and inspection data for the testing apparatus. The data acquisition unit is generally comprised of a computer, a keyboard, a video display monitor, software and electronic interconnections to the computer control unit and to the mill roll sensor apparatus. Evaluation and disposition of each mill roll is performed by employing data received from non-destructive testing of each mill roll. During operation of the mill roll apparatus, an alarm indication is displayed to the apparatus operator if a signal which is outside of the stored control limits is received from the EMAT receiver coil. Additionally, apparatus or process parameters may be automatically re-adjusted through computer control. The data acquisition unit collects and archives empirical data that may be used for later post-analysis, historical tracking and process monitoring.

The present invention also has safeguards for EMAT receiver coil and transmitter from the effects of certain undesirable electrical interference. The present invention includes an electrostatic shield which acts as a barrier to protect the EMAT receiver coil from Electromagnetic Interference and Radio Frequency Interference (EMI/RFI) which have been shown to pose significant problems in using EMAT instrumentation in an industrial environment where welders, grinders and other manufacturing equipment can generate deleterious electrical interference. The electrostatic shield significantly improves the performance and reliability of non-destructive testing of mill roll cracks by reducing unwanted interference and by increasing test sensitivity.

The various features of novelty which characterize the present invention are pointed out with particularity in the claims annexed to and forming a part of this disclosure. For a better understanding of the present invention, its operation advantages and specific objects attained by its uses, reference is made to the accompanying drawings and descriptive matter in which the preferred embodiment of the invention is illustrated.

BRIEF DESCRIPTION OF THE DRAWINGS

In the drawings:

FIG. 4 is an expanded top view of the EMAT inspection head seen in FIG. 2; and

FIG. 5 is an expanded side view of the EMAT inspection head seen in FIG. 2.

DETAILED DESCRIPTION OF THE PREFERRED EMBODIMENT

The present invention permits automated inspection of mill rolls. A typical sheet metal production and treatment line on which the present invention may be utilized is comprised of a rolling mill, a plurality of roughing stands, a plurality of finishing stands, a first shearing apparatus, a welding apparatus, a temper mill, a pickling apparatus, a water rinse apparatus, a drying apparatus, a second shearing apparatus, a side slitter apparatus and a tandem cold mill. Frequently, a long flat sheet of metal produced by the rolling mill will be wound into a coil after passing through the finishing stands. Both hot and cold rolling operations require mill rolls to remove the gauge of the sheet metal. These mill rolls are frequently removed from production and refurbished on grinding machines to remove cracks, harden surface and local soft spots. It is during grinding cycles that mill roll inspection is best performed.

The quality and integrity of steel mill rolls are key factors in the productivity of steel production facilities and the quality of the finished product.

Mill rolls are subject to extreme operating conditions which are known to cause "firecracking" and "spalling". Reliable detection of firecracks with the "Automated Mill Roll Inspection System" of the present invention provides the assurance that defective roll conditions are identified prior to return to service in the rolling mill.

The system provides a fully automated mill roll inspection system which:

- rapidly identifies surface breaking and sub-surface defects in steel mill rolls by using proven non-destructive Electro Magnetic Acoustic Transducer (EMAT) inspection technology.
- provides immediate roll disposition including a detailed defect map indicating the number, location and relative severity of defects detected.
- is easily retrofit onto any style or type of sheet metal roll grinding or machining equipment.
- is compatible with all types of steel work, intermediate and backup rolls.

The system replaces the need for conventional eddy current and ultrasonic inspection systems by combining the ability to detect both surface breaking and sub-surface flaws into one inspection operation. EMAT technology permits an extremely fast roll inspection cycle time, typically within two minutes.

EMAT's provide the ability to rapidly perform repeated inspections without the need for calibration, use of couplant or frequent transducer changes.

The system is configured to interface with line control systems and plant-wide host systems for automatic download of roll identification information and upload of inspection results.

Figure 1:
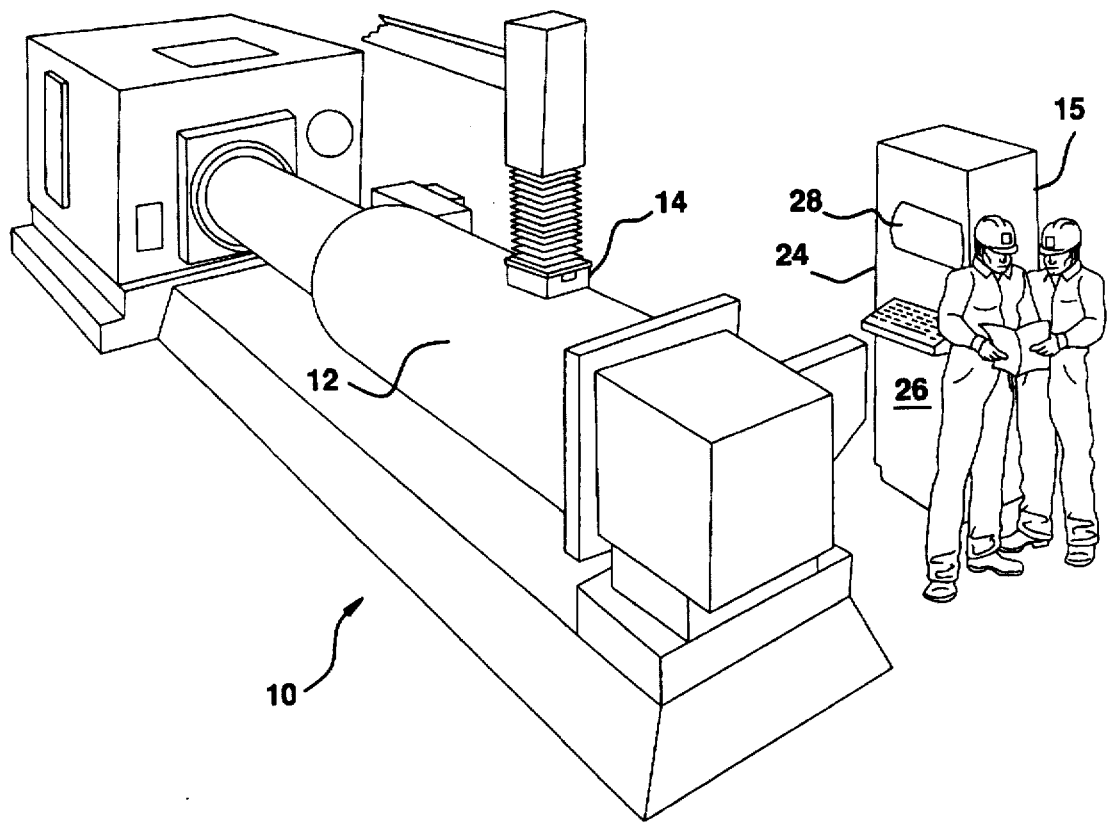
FIG. 1 is a perspective view of a mill roll station showing the mill roll crack inspection system with the EMAT mounted to translate along the mill roll surface and the remote control and data acquisition system proximate to the mill roll station.
Figure 2:
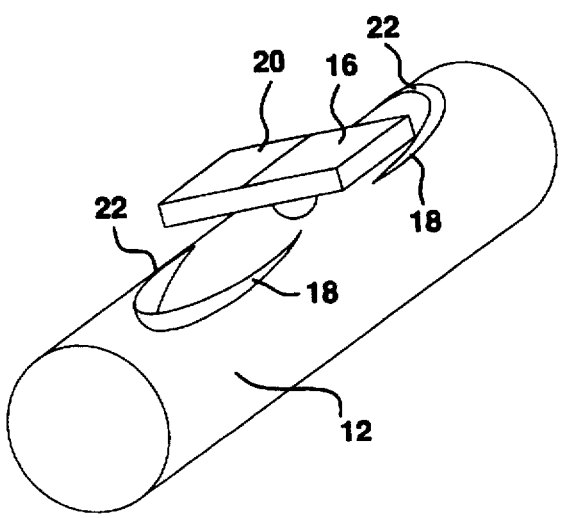
FIG. 2 is an expanded view of the mill roll showing the mounting of the EMAT inspection unit mounted to translate along the roll.

FIGS. 1 and 2 show a mill roll grinding station (10) having a mill roll 12) with a EMAT defect inspection assembly (14) mounted to translate along the surface of the roll (12) which is controlled by a data acquisition and control assembly (15) which may be located in the area of the mill roll grinding station (10) The assembly (14) has a transmitter coil (16) which produces an ultrasonic surface wave (18) which propagates into the roll (12). The wave is attenuated if roll defects are present and the receiver coil (20) experiences a loss or signal indicating the defect.

The assembly (15) has a computer control unit (24) which is in electrical communication with the mill roll (10) grinding station and a data acquisition unit (26). A first cable (not shown) provides the electrical connection between the computer control unit (24) and the roll inspection apparatus.

At the conclusion of the grinding or machining operation on the roll (12), the EMAT sensor assembly (14) rapidly translates the length of the roll as it is rotated. It provides nearly 100% inspection of the roll surface. Instantaneously, upon completion of a single scan, a good/bad signal is presented to the operator at the operator interface grinder and a detailed defect map is displayed at the console (28). The defect map indicates the individual defects, size, severity and location along the roll length and circumference. An inspection results contain a summary of the number and severity of defects.

Immediate disposition of the roll quality is provided to the operator as an easy to read defect map and inspection summary. Color display is used to indicate the size and severity of defects revealed during inspection. The results of each inspection are catalogued and stored within the system (15) and are uniquely traceable to each mill roll. This data can be recalled and displayed for post inspection evaluation.

It should be remembered that the system (15) includes two inspection modes; fine and deep. The fine mode employs an ultrasonic frequency ranging from about 4 to 6 MHz with a preferred frequency of about 5.6 MHz. The deep mode employs a frequency ranging from about 400 to 500 KHz with a preferred frequency of about 485 KHz. The preferred angle of incidence is about 30° to roll axis for sensitivity to both circumferential and longitudinal defects.

The fine mode detects surface and near surface type defects with a minimum size of 0.100" (2.5 mm) length by 0.005" (125 μm) depth. The deep mode detects surface and internal defects, with minimum size 0.100" (2.5 mm) length by 0.030" (750 μm) depth, down to 0.250" (6 mm) below the roll surface. Thus the deep mode is first used to see if the roll (12) has to be removed for repair by lathe operation. If there are no deep defects, the system is switched to a fine mode for detecting surface cracks which can be removed by the next grinding operation.

Figure 3:
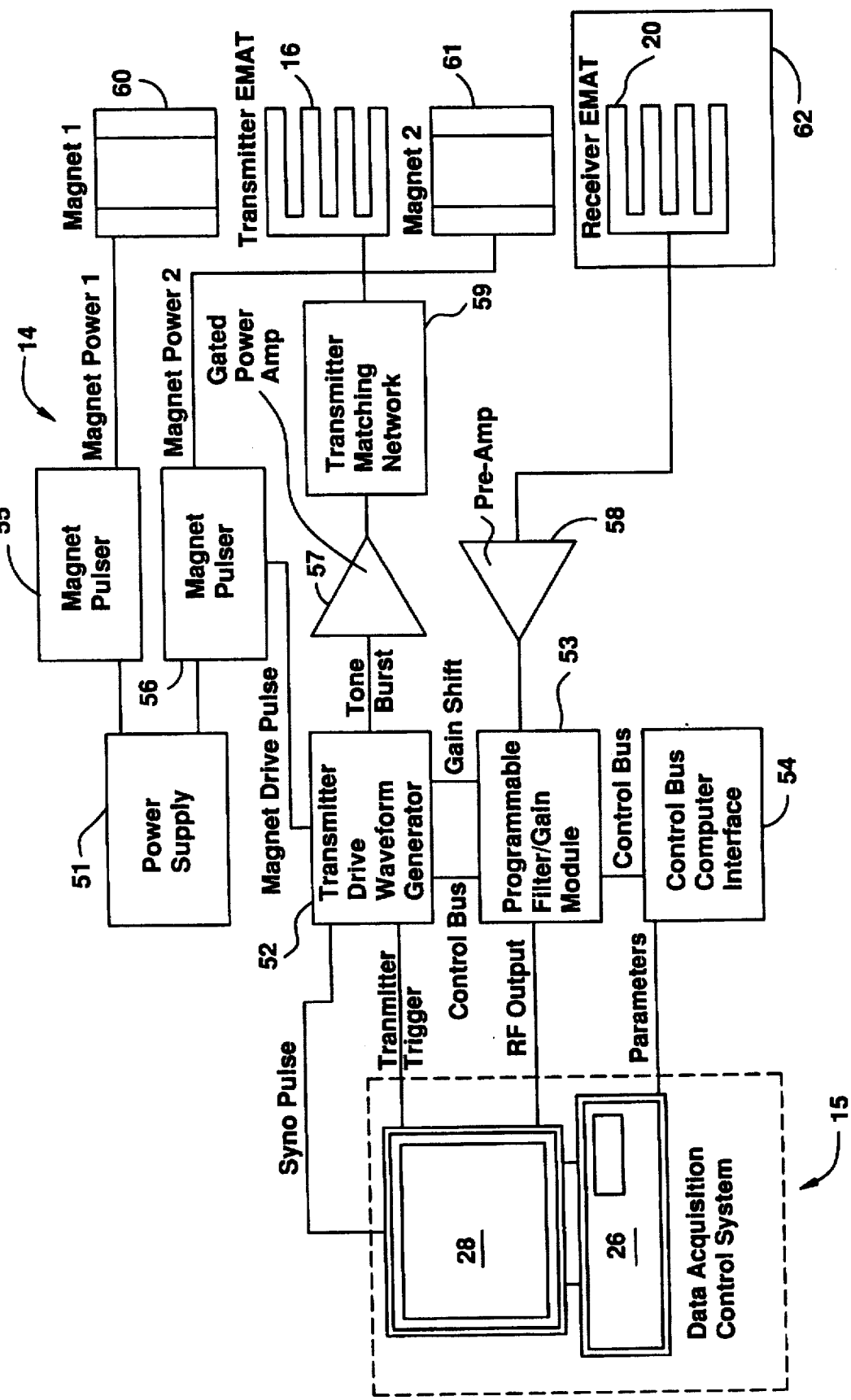
FIG. 3 is a schematic drawing of the electronics employed with the EMAT transmitter and receiver coil of the present invention.

FIG. 3 provides a schematic illustration of the electronics employed with EMAT assembly (14)—transmitting coil (16) and the EMAT receiver coil (20). The electronics include a power supply (51), a transmitter drive wave-form generator (52), a programmable filter/gain module (53), a control bus computer interface (54), a first magnet pulser (55), a second magnet pulser (56), a gated power amp (57), a pre-amp (58), a transmitter matching network (59), a first magnet (60), a second magnet (61) and an electrostatic shield (62). The power supply (51) provides electric current to the first magnet pulser (55) and to the second magnet pulser (56). The first magnet pulser (55) is connected to first magnet (60), and the second magnet pulser (56) is linked to second magnet (61). First magnet pulser (55) and second magnet pulser 56) generate high current pulses which are employed to charge first magnet (60) and second magnet (61), respectively.

The transmitter drive waveform generator (52) is linked electrically to the data acquisition unit (33), the second magnet pulser (56), the gated power amp (57) and the programmable filter/gain module (53). A sync pulse and a transmitter trigger are provided to the transmitter wave form generator (52) from the data acquisition unit (15). From the transmitter wave form generator (52), a magnet drive pulse is provided to the second magnet pulser (56). A tone burst is provided to the gated power amp (57) and a gain shift is supplied to the programmable filter/gain module (53).

In addition to being linked to the transmitter drive waveform generator (52), the programmable filter/gain module (53) is in electrical communication with the data acquisition unit (15), the pre-amp (58) and the control bus computer interface (54). The programmable filter/gain module (53), a control bus is provided from the control bus computer interface (54). A RF output is supplied from the programmable filter/gain module (53) to the data acquisition unit (15).

The control bus computer interface (54), in addition to having an electrical connection with the programmable filter/gain module (53), has an electrical link to the data acquisition unit (15). EMAT system parameters which have been stored on the data acquisition unit (15) are provided to the control bus computer interface (54).

The gated power amp (57) is joined to the transmitter matching network (59) which is in turn linked to the EMAT transmitter coil (16).

The pre-amp (58) is in electrical communication with the EMAT receiver coil (20) which is located within an electrostatic shield (62) and which receives the transmitted surface wave (22) from the roll (12). The pre-amp (58) and the transmitter matching network (59) enable the EMAT coils (16, 20) to be operated at distances greater than 100 feet from other electronic instrumentation of the present invention.

Turning next to FIGS. 4 and 5, it will be seen that the EMAT assembly 14 has a pair of oppositely located wheels (64, 66) suitable for rolling along the surface of the roll (12). Also a pair of quick connect disconnect electrical connections (68, 70). Similarly a quick disconnect mechanical assembly (72) is provided for removing the assembly (15) from the roll (12).

Returning to FIGS. 1 and 2, the EMAT assembly (14) scans the mill roll moving from side to side as the roll rotates. The EMAT assembly may be manually driven to scan if a particular area of the roll requires a closer examination.

While a specific embodiment of the invention has been shown and described in detail to illustrate the application of the principles of the invention, it will be understood that the invention may be embodied otherwise without departing from such principles.

What is claimed is:

1. An automated mill roll inspection system for non-destructively examining a forged or cast steel roll for surface and sub-surface defects, the inspection system comprising:

a first electromagnetic acoustic transducer movably mounted on a metal mill roll, said first electromagnetic acoustic transducer propagating an ultrasonic surface wave into the metal roll;

a second electromagnetic acoustic transducer movably mounted on a metal mill roll, said second electromagnetic acoustic transducer receiving the propagated ultrasonic surface wave;

a first surface wave generator for producing a first surface wave frequency for detecting surface defects in the mill roll;

a second surface wave generator for producing a second surface wave frequency for detecting sub-surface defects in the mill roll, wherein said second surface wave frequency is different from said first surface wave frequency;

a computer control unit connected to and in communication with said first and second electromagnetic acoustic transducers for coordinating first the inspection of the metal roll for surface defects and then for sub-surface defects; and a data acquisition unit connected to and in communication with said computer control unit for receiving, storing, displaying and analyzing information provided from said computer control unit and for transmitting information thereto, said data acquisition unit detecting an surface and sub-surface defects in the metal mill roll based on changes in the ultrasonic surface waves.

2. A system according to claim 1, wherein the electromagnetic acoustic transducers includes an electrostatic shield for protecting the second electromagnetic acoustic transducer from electromagnetic interference and radio frequency interference.

3. A system according to claim 1, wherein the first electromagnetic acoustic transducer and the second electromagnetic acoustic transducer include an electromagnet which is in electrical communication with a magnet pulser which produces high current pulses of electrical energy that is used to charge the electromagnets.

4. A system according to claim 1, wherein said first and second electromagnetic acoustic transducers are positioned in an assembly pivotally attached to means for moving the assembly for scanning the metal mill roll lengthwise for defects.

5. A system according to claim 4, wherein said electromagnetic acoustic transducers operate in two modes for crack detection, wherein the first mode of said two modes utilizes said first surface wave frequency and the second mode of said two modes utilizes said second surface wave frequency.

6. A system according to claim 5, wherein said first mode detects cracks in the top about 0.020 inch of the metal mill roll and the second mode detects cracks up to about 0.250 inch of the metal mill roll.

7. A method of inspecting a mill roll for surface and sub-surface defects, comprising the steps of:

propagating a first ultrasonic surface wave into a mill roll with a first electromagnetic acoustic transducer at a first surface wave frequency for detecting a surface defect;

receiving the first propagated ultrasonic surface wave from the mill roll with a second electromagnetic acoustic transducer;

generating a transmitted and a received signal from said first and second electromagnetic acoustic transducers with data acquisition means connected to said electromagnetic acoustic transducers;

determining from the transmitted and received signals any surface defects in the mill roll with a computer control unit;

displaying information regarding any defects in the mill roll; and repeating the above steps with a second ultrasonic surface wave at a second surface wave frequency for detecting any sub-surface defects, wherein said second surface wave frequency is different from said first surface wave frequency.

8. A method according to claim 7, further comprising the step of scanning the mill roll.

* * * * *